(12) United States Patent
Kim et al.

(10) Patent No.: US 8,234,094 B2
(45) Date of Patent: Jul. 31, 2012

(54) SYSTEM AND METHOD FOR TESTING LIQUID CRYSTAL DISPLAY DEVICE

(75) Inventors: Ja-Geun Kim, Seoul (KR); Jin-Tae Gil, Paju-si (KR); Sang-Ho Nam, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 346 days.

(21) Appl. No.: 12/631,950

(22) Filed: Dec. 7, 2009

(65) Prior Publication Data

US 2010/0250193 A1 Sep. 30, 2010

(51) Int. Cl.
*G06F 15/00* (2006.01)
*G06K 9/00* (2006.01)
(52) U.S. Cl. ........................................ 702/182; 382/149
(58) Field of Classification Search .................. 702/182; 382/149; 356/239.2; 345/87; 324/770
See application file for complete search history.

(56) References Cited

U.S. PATENT DOCUMENTS

| 7,800,568 | B2 * | 9/2010 | Kang et al. | 345/87 |
| 7,868,644 | B2 * | 1/2011 | Kang et al. | 324/760.02 |
| 2009/0290785 | A1 * | 11/2009 | Kang et al. | 382/149 |

* cited by examiner

*Primary Examiner* — Bryan Bui
(74) *Attorney, Agent, or Firm* — Brinks Hofer Gilson & Lione (57) ABSTRACT

A system for testing a liquid crystal display (LCD) device includes a testing device photographing and capturing an image of a defect generated on a substrate having a thin film array formed thereon, the testing device providing testing information on the defect, a ARPC automatically determining defectiveness of the substrate by an automatic determination method using a defect determining automation program designed based on a testing worker's determination method and behavior aspect, the captured image and the testing information on the defect, a PRPC determining defectiveness of the substrate based on the captured image and the testing information on the defect, if the defectiveness of the substrate is undeterminable by the ARPC, and a main server connecting the ARPC with the PRPC and storing the captured image and the testing information on the defect. The ARPC extracts characteristics of the defect by using the testing information on the defect and the ARPC analyzes the extracted characteristics of the defect to classify and calculate the degree of the defect.

10 Claims, 4 Drawing Sheets

SYSTEM AND METHOD FOR TESTING LIQUID CRYSTAL DISPLAY DEVICE

CROSS REFERENCE TO RELATED APPLICATION

This application claims the benefit of the Patent Korean Application No. 10-2009-0027293, filed on Mar. 31, 2009, which is hereby incorporated by reference as if fully set forth herein.

BACKGROUND OF THE DISCLOSURE

1. Field of the Disclosure

The present disclosure relates to a liquid crystal display device, more particularly, to a system and method for testing a liquid crystal display device which is able to automatically determine whether a thin transistor array substrate and a color filter array substrate are malfunction ones based on an automatic malfunction determining system in order to reduce the time and the number of workers required for malfunction testing and to improve success rate of malfunction determination.

2. Discussion of the Related Art

With rising public interest in information display, research, studies and commercialization for flat panel display (FPD) devices have been in progress. Especially, liquid crystal display (LCD) devices of such FPD devices require optically anisotropic liquid to present an image and the LCD devices are good in resolution, color display and image quality such that they may be applied in laptop computers or desktop computer monitors actively.

The LCD device may include a thin film transistor (TFT) array substrate, color filter substrate and liquid crystal layer formed between the TFT array substrate and the color filter substrate.

Here, the TFT array substrate includes gate and data lines, TFTs and pixel electrodes. The gate and data lines are arranged on the TFT array substrate horizontally and vertically to define a pixel area. The TFT is formed in each area formed by the gate and data lines as switching element crossed each other and the pixel electrode is formed in the pixel area.

The color filter substrate includes a color filter and a black matrix. The color filter is configured of sub-color filters, for example, R, G and B. The black matrix divides the color filter into the sub-color filters to define the pixel area and it cuts off light transmitting the liquid crystal layer. In addition, the color filter substrates may include a transparent common electrode applying common voltage to the liquid crystal layer. Here, the common electrode may be formed on the TFT array substrate.

The TFT array substrate and the color substrate having the above configuration are attached to each other by sealant to be a liquid crystal display panel.

This liquid crystal display device may be manufactured through an TFT array process, a color filter process, a cell process and a module process.

First, in the TFT array process, photolithography and etching are repeated such that the TFT array may be formed on a first substrate that is a transparent insulating substrate. In the color filter process, the black matrix is formed on a second substrate that is a transparent insulating substrate to cut off light except the pixel areas and color filters of red (R), green (G) and blue (B) are formed by using dye or pigment.

Prior to the cell process, an auxiliary process of testing the array and color filter substrate to detect a defect is necessary is to check the state of TFT array and color filter substrates.

In the cell process, the TFT array substrate and the color filter substrate are attached to each other by a sealant and here a predetermined cell gap is maintained between the TFT array substrate and the color filter substrate. Before or after attaching the substrates, liquid crystal is formed between the first and second substrates to form a liquid crystal display panel cell.

In the module process, a circuit for processing signals is connected with the LCD panel by using mount technology that is well-known knowledge in this art to be installed in a framework of an apparatus to manufacture a LCD module.

The testing process of the TFT array and color filter substrates prior to the cell process as mentioned above is performed to detect whether the TFT array and color filter substrates are detective in exterior appearance or electrically, for example, whether there is color filter grind, oblique blemish, rubbing line, pin hole and open or short of the gate/data line.

A testing system of the related art includes a testing unit for detecting defectiveness of the TFT array substrate or color filter substrate and a repair system for repairing the defectiveness in case that there is the defectiveness of the substrate based on the result of the testing.

The testing unit includes a testing device, a system computer and a monitor. The testing device tests the TFT array substrate or color filter substrate to detect defectiveness. The system computer operates the testing device and the system computer is connected with the monitor. A keyboard and mouse are connected with the system computer to operate the system computer and a review monitor is mounted in the testing device such that a worker may identify defectiveness of the substrate via the review monitor.

According to the testing system of the related art, a single review monitor is connected with the repair computer in one-to-one such that a testing worker may control the single testing device. However, the above testing system of the related art has a disadvantage that the testing device is not operated during the lunch break or rest of the worker and this might result in time loss and work deterioration. In addition, the testing system of the related art requires testing workers as many as the testing devices.

SUMMARY OF THE DISCLOSURE

Accordingly, the present invention is directed to a method and system for testing a LCD device.

A system for testing a liquid crystal display (LCD) device includes a testing device photographing and capturing an image of a defect generated on a substrate having a thin film array formed thereon, the testing device providing testing information on the defect; a ARPC automatically determining defectiveness of the substrate by an automatic determination method using a defect determining automation program designed based on a testing worker's determination method and behavior aspect, the captured image and the testing information on the defect; a PRPC determining defectiveness of the substrate based on the captured image and the information on the defect, if the defectiveness of the substrate is undeterminable by the ARPC; and a main server connecting the ARPC with the PRPC and storing the captured image and the testing information on the defect, wherein the ARPC extracts characteristics of the defect by using the testing information on the defect and the ARPC analyzes the extracted characteristics of the defect to classify and calculate the degree of the defect.

In case that it is determined that the degree of the defect is repairable by the ARPC, the testing device may repair the defect.

The ARPC may determine whether the defect is repairable by the testing device.

In another aspect of the present invention, a method of testing a LCD device comprising steps of: photographing a defect generated in a substrate having a thin film array formed thereon and capturing an image of the photographed defect; determining reliability of the captured image; reviewing the defect and extracting characteristics of the defect, if it is determined that the captured image is reliable; analyzing the extracted characteristics of the defect by a defect determining automation program designed based on a testing worker's determination method and behavior aspect, and classifying and calculating degree of the defect; determining based on the result of the calculation whether the defectiveness of the substrate is determinable by the automatic determination method; determining the defectiveness of the substrate by the automatic determination method if the defectiveness of the substrate is determinable by the automatic determination method; and determining the defectiveness of the substrate by a passive determination method if the defectiveness of the substrate is undeterminable by the automatic determination method.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the disclosure and are incorporated in and constitute a part of this application, illustrate embodiment(s) of the disclosure and together with the description serve to explain the principle of the disclosure.

In the drawings.

DESCRIPTION OF EXEMPLARY EMBODIMENTS

Reference will now be made in detail to the specific embodiments of the present invention, examples of which are illustrated in the accompanying drawings. Wherever possible, the same reference numbers will be used throughout the drawings to refer to the same or like parts.

Figure 1:
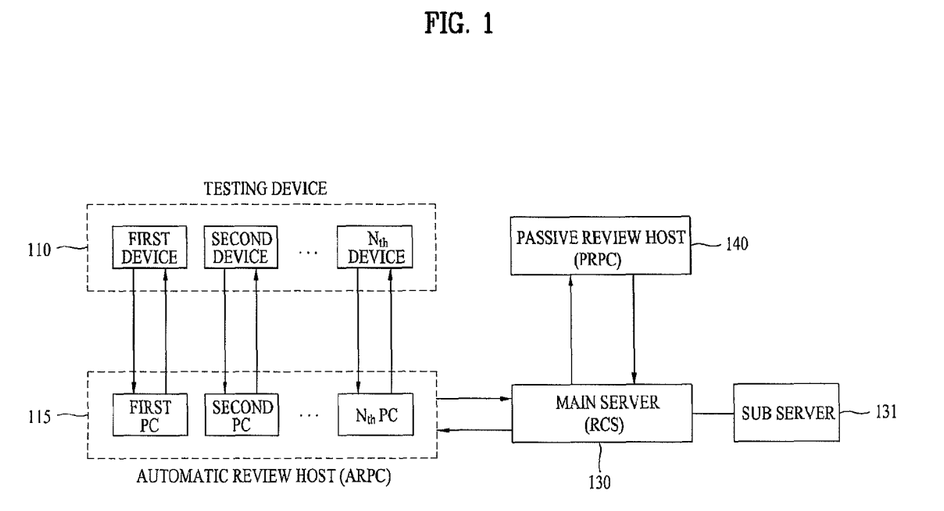
FIG. 1 is a diagram illustrating a testing system of a LCD device according to an exemplary embodiment of the present disclosure.

FIG. 1 illustrates a testing system of a LCD device according to an exemplary embodiment of the present disclosure.

The testing system shown in FIG. 1 includes a testing device 110, an automatic review (or determination) host (ARPC) 115, a main server 130 and a passive review host (PRPC) 140.

The ARPC 115 and the PRPC 140 are connected to the main server 130 in a direct network, respectively. The testing device 110 is connected in a separate network. Here, the hosts 115 and 140 may be embodied as personal computers.

The testing device 110 includes a first testing device to nth testing device. Each of the first to nth testing devices includes a vision part and a computer system. In the vision part may be installed a camera to detect a pattern of the substrate. The computer system analyzes a signal input in the camera.

Here, the cameral scans the panel in a horizontal direction and it collects testing patterns displayed on the array substrate and the color filter substrate. Hence, the camera transmits the collected testing patterns to the computer system. To complement different defect detecting according to view angles, testing is performed in a range of predetermined angles, for example, 0°~70°, 80°~100° and 110°~160° such that efficiency of the defective detecting may be improved. As a vision device such as the camera is installed the testing device 110, the limit of the conventional testing that uses worker's eyes may be overcome and this can create improved work efficiency and improved productivity. Moreover, the vision device may be manufactured with periodically upgradable optical technology, new versions and new image file versions, such that reliability of the result of the defectiveness detecting may be enhanced.

The testing device 110 has a function of automatic defect repair (ADR) to automatically repair a defect of the substrate according to a command of the main server or the result of the automatic testing transmitted by the ARPC 115.

The ARPC 115 may be configured of a first to nth personal computer corresponding to the first and n device of the testing device 110. The testing device 110 transmits an image file of captured defect, defect information and the testing device number to the ARPC 115. Then, after checking the state of the defect, the APRC 115 performs the automatic defect determination and it commands the testing device to repair the defect.

The ARPC 115 will be described more specifically as follows. To detect and determine various kinds defects automatically, the ARPC 115 examines the image file captured by the testing device 110 and it extracts characteristics of the defect, for example, the size, position, shape and position relation with adjacent patterns.

Also, the testing worker's testing methods and the aspects of the testing worker's behavior, which are performed passively in the conventional art, are mechanically transformed and their designed algorithm is programmed (hereinafter, 'defect determining automation program' for convenience sake). The defect determining automation program according to the present invention is a program in that the extracted characteristics of the defect are analyzed to classify and calculate degree of the defect, not a passive method of determining the degree of the defect.

The ARPC 115 automatically classifies and calculates the degree of detect based on the extracted characteristics of the defects. Then, the ARPC 115 automatically determines whether there is a defect in the substrate based on the result of the calculation.

Here, according to the automatic determination method of the substrate defect, it is determined based on the result of the calculation whether the defect of the substrates is determinable by the automatic defect determination method by using the result of the defect. If it is determined that the defect is determinable by the automatic determination method, the degree of the defect is determined and it is determined whether the defect is repairable by the automatic defect repair. If it is determined that the defect is repairable, the ARPC 115 controls the testing device to repair the defect. If it is determined that the defect of the substrate is undeterminable by using the automatic determination method, the image file of the captured defect, the defect information and the testing device number are transmitted to the main server 130. Here, the degree of the defect that is undeterminable by the defect determining automation program is determined by the passive determination method and the cause of the defect determined by the passive determination method is upgraded to the defect determining automation program afterward. As a result, if the defect requiring the passive determination method is generated again, the defect may be determinable by the automatic determination method.

If the ARPC 115 cannot determine whether there is a defect in the substrates by the automatic determination method, the main server 130 receives the image file of the defects, ID of the array or color filter substrate, ID of the glass substrate, the defect number, the testing device number and the like from the ARPC 115 and it stores this information in a database. After that, the main server 130 transmits the information to the PRPC 140. At this time, a sub-server 131 may be installed rather than the main server 130 to operate in case of unexpected emergency. That is, if the main server 130 is down, the sub-server 131 is useable instead of the main server 130.

If the ARPC 115 cannot determine the defectiveness of the substrate by using the automatic determination method, the worker directly checks the PRPC 140 to check the state of the defect by using the image file of the defect. Then, the worker determines whether there is the defect in the substrate and calculates a determination value of the defect. The calculated value is transmitted to the main server 130 and it is stored in the database.

The testing system of the LCD device having the above configuration includes the ARPC 115 configured of the first to nth PC corresponding to the first to nth device of the testing device 110. the ARPC 115 extracts the characteristics of the detect by using the image file of the defect and it automatically determines whether there is a defect of the substrate by using the extracted characteristics such that the defect may be repaired immediately based on the result of the determination.

As a result, compared with the conventional passive determination method, the testing time and the number of the testing workers may be reduced. In addition, testing success rate may increase remarkably because the defect is determined by the automatic determination method, not the passive determination method performed by the workers, such that reliability of defect testing may be improved.

In the meanwhile, each of the hosts 115, 120 and 140 according to the embodiment of the present invention is embodied in a remote place and it may control the testing device by a remote control.

Figure 2:
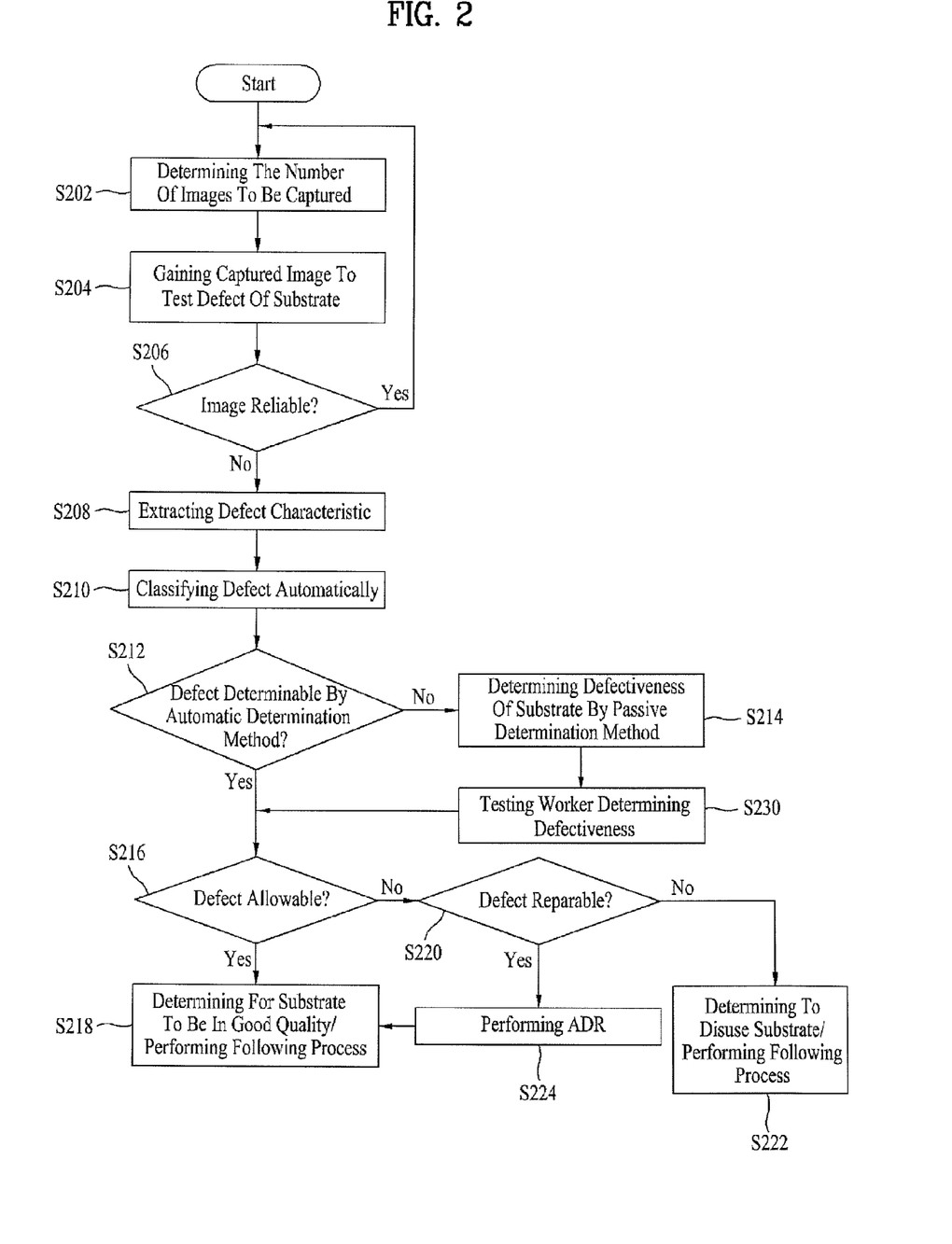
FIG. 2 is a flow chart illustrating a method of testing the LCD device.

FIG. 2 is a flow chart illustrating a testing method of the LCD device according to the exemplary embodiment of the present invention.

In reference to FIG. 2, once the substrate having the TFT array or the color filter array formed thereon is loaded, it is tested by the testing device 110 whether there is a defect in the TFT array substrate or the color filter array substrate. If sensing the defect in the TFT array substrate or the color filter array substrate, the testing device 110 determines the number of images which will be captured according to the state of the defect (S202). Here, the number of the images which will be captured is commonly in proportion to the number or size of foreign substances causing the defect. Hence, the testing device 110 captures the images of the sensed defect (S204).

The testing device 110 determines whether the captured image is reliable enough to check the state of the defect (S206).

If it is determined that the captured image is unreliable, the sensed defect is captured again. If it is determined that the capture image is reliable, the testing device 110 transmits the captured image file, the defect information and the testing number to the ARPC 115 automatically.

After receiving the captured image file of the defect, the defect information and the testing device number, the ARPC 115 examines the image file and it extracts the characteristics of the defect (S208). The extracted characteristics of the defect are analyzed by the defect determining automation program and the degree of defect is classified (S210) and then numerical values of the degree is calculated.

The ARPC 115 determines based on the result of the calculation of the degree numerically whether the defect of the substrate is determinable by the automatic determination method (S212).

If it is determined that the defect of the substrate is undeterminable by the automatic determination method, it is determined by using the passive determination method whether there is a defect in the substrate (S214).

If it is determined that the defect of the substrate is determinable by the automatic determination method, it is determined whether the degree of the defect generated in the array or color filter substrate is minute enough to be determined allowable (S216).

If it is determined that the degree of the defect is minute enough to be allowable based on the determination, it is determined the substrate is allowable and a following process is performed (S220).

If it is determined that the defect is irreparable by the automatic defect repair (ADR), it is determined that the substrate is defective and a following process is performed (S222). If it is determined that the defect is repairable, the defect generated in the substrate is automatically repaired (ADR) by the testing device 110 (S224). Here, the testing device 110 captures the image of the area having the ADR performed therein and the ARPC 115 determines whether the repair of the defect is performed successfully, that is, whether the ADR is performed successfully. If there is the defect even after the defect is repaired by the testing device 110, that is, if the ADR is not performed successfully, the ADR is repeated by the testing device 110. Hence, once the defect is repaired, it is determined the substrate is allowably in good quality and the following process is performed (S218). Here, the following process after determining that the substrate is defective may be a case of abolishing the defective substrate.

If the defectiveness of the substrate is undeterminable by the automatic determination method, the defectiveness of the substrate is determined by the passive determination method (S214). Specifically, if it is determined that the defectiveness of the substrate is undeterminable by the automatic determination method in S212, the ARPC 115 transmits the captured defect image file, the defect information and the testing device number to the main server 130. Hence, the main server 130 transmits them to the PRPC 140. The PRPC 140 reviews and determines the defectiveness based on the captured defect image file (S230). That is, the worker opens the captured image file of the defect and reviews the defect to make determination of the defectiveness.

If the degree of the defect is allowable based on the result of the determination performed by the worker passively, it is determined that the substrate is in good quality and the following process is performed (S218). If the degree of the defect is not allowable, it is determined whether the defect is repairable (S220). If the defect is repairable, the information is transmitted to the main server 130 and the main server 130 transmits the information to the testing device 110 such that the testing device performs ADR for the corresponding defect.

Hence, the testing device 110 captures an image of the area having the ADR performed therein and the ARPC 115 determines whether the repair for the defect is performed successfully, that is, the ADR for the defect is successful. If the defect remains even after the ADR performed by the testing device 110, that is, it is determined that the ADR is not successful, the ADR is repeated by the testing device 110.

Most defects are determined by the automatic determination method performed by the ARPC 115 and the defect is repaired under the control of the ARPC 115. Here, for only some cases, the passive determination method is performed by the PRPC 140. The information on the defect requiring the passive determination is transmitted to the ARPC 115 such that the defect determining automation program may be upgraded. As a result, the cases that are undeterminable by the ARPC 115 may be reduced and the times of the passive determination performed by the PRPC 140 may be reduced accordingly.

According to the testing system of the LCD device according to the exemplary embodiment of the present invention, it may be determinable automatically whether the substrate is defective by using the ARPC 115 configured of the first to n PC corresponding to the first and n testing device. Only if a defect undeterminable by the automatic determination method of the ARPC 115 is generated, the passive determination method of the PRPC 140 is performed. As a result, compared with the conventional passive testing system, the testing time and the number of the testing workers may be reduced remarkably. In addition, test success rate may increase noticeably because the defectiveness of the substrate is determined by using the automatic determination method, not the passive determination method by the testing workers. Accordingly, reliability of defect testing may be improved.

Figure 3:
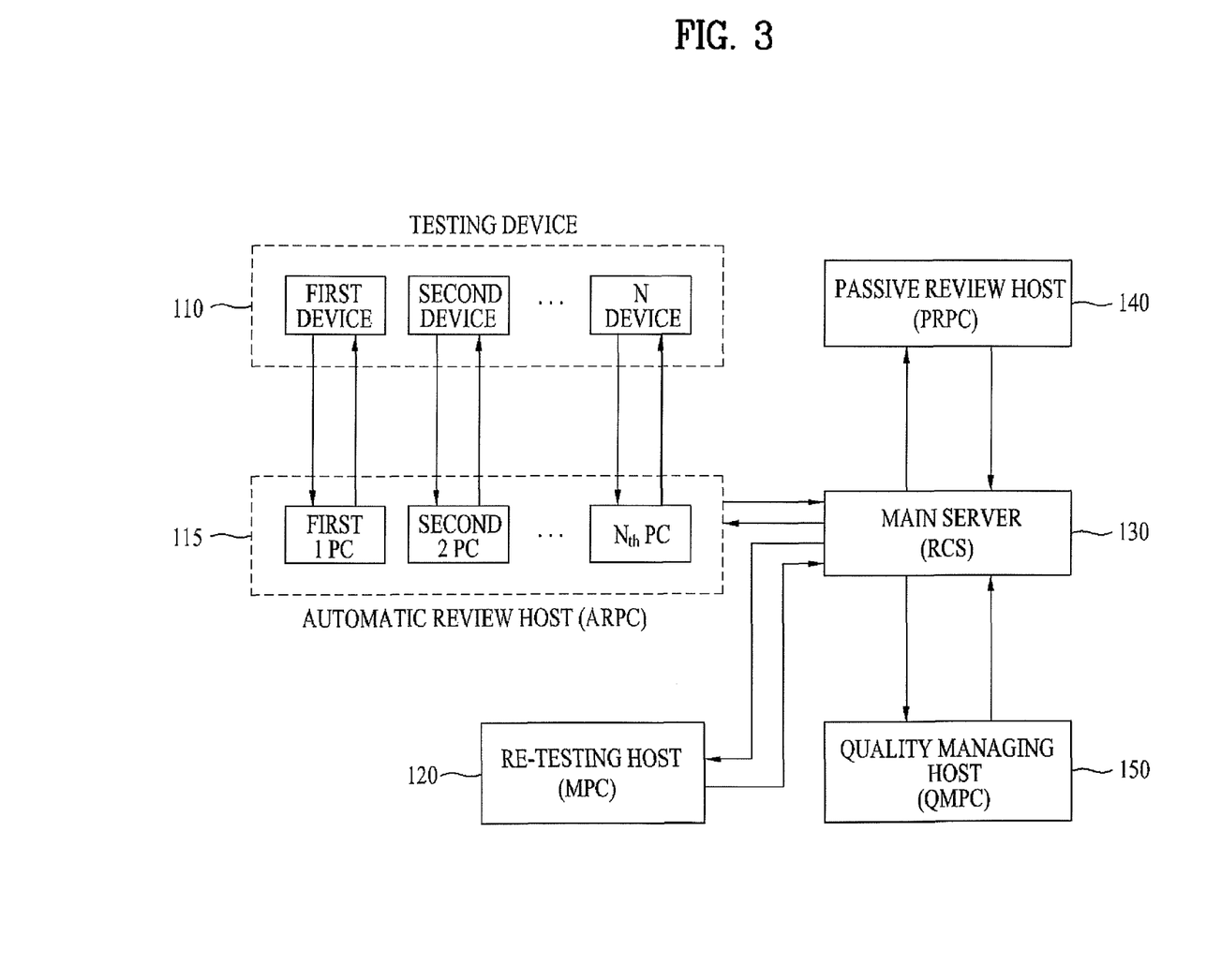
FIG. 3 is a diagram illustrating a testing system of a LCD device according to another embodiment of the present disclosure.

FIG. 3 is a diagram illustrating a testing system of a LCD device according to another embodiment of the present invention.

In reference to FIG. 3, a testing system 100 according to this embodiment of the present invention includes a testing device 110, an automatic review (or determination) host (ARPC) 115, a main server (RSC) 130, a passive review host (PRPC) 140, a re-testing host (MPC) 120 and a quality managing host (QPC) 150. That is, compared with the testing system according to the above embodiment, the testing system 100 according to this embodiment of the present invention further includes the MPC 120 and QPC 150.

If the defectiveness of the substrate is undeterminable by the automatic determination method of the ARPC 115 and the passive determination method of PRPC 140, the MPC 120 re-tests whether there is a defect in the substrate. Here, the MPC 120 reviews and determines defectiveness of the substrate based on images photographed by a camera of the testing device 110 in real-time, not on the captured image of the defects. The review and determination of the MPC 120 may be a final testing.

Once the ADP is performed by the testing device 110, the QPC 150 determines whether the repair is performed successfully based on the captured image information of the area having the ADR performed therein.

According to the above embodiment, it is determined by the ARPC 115 whether the ADR is performed successfully. In contrast, according to this embodiment, the QPC 150 is further provided to relive the load of the ARPC 115 and the QPC 150 determines whether the ADR is performed successfully.

Figure 4:
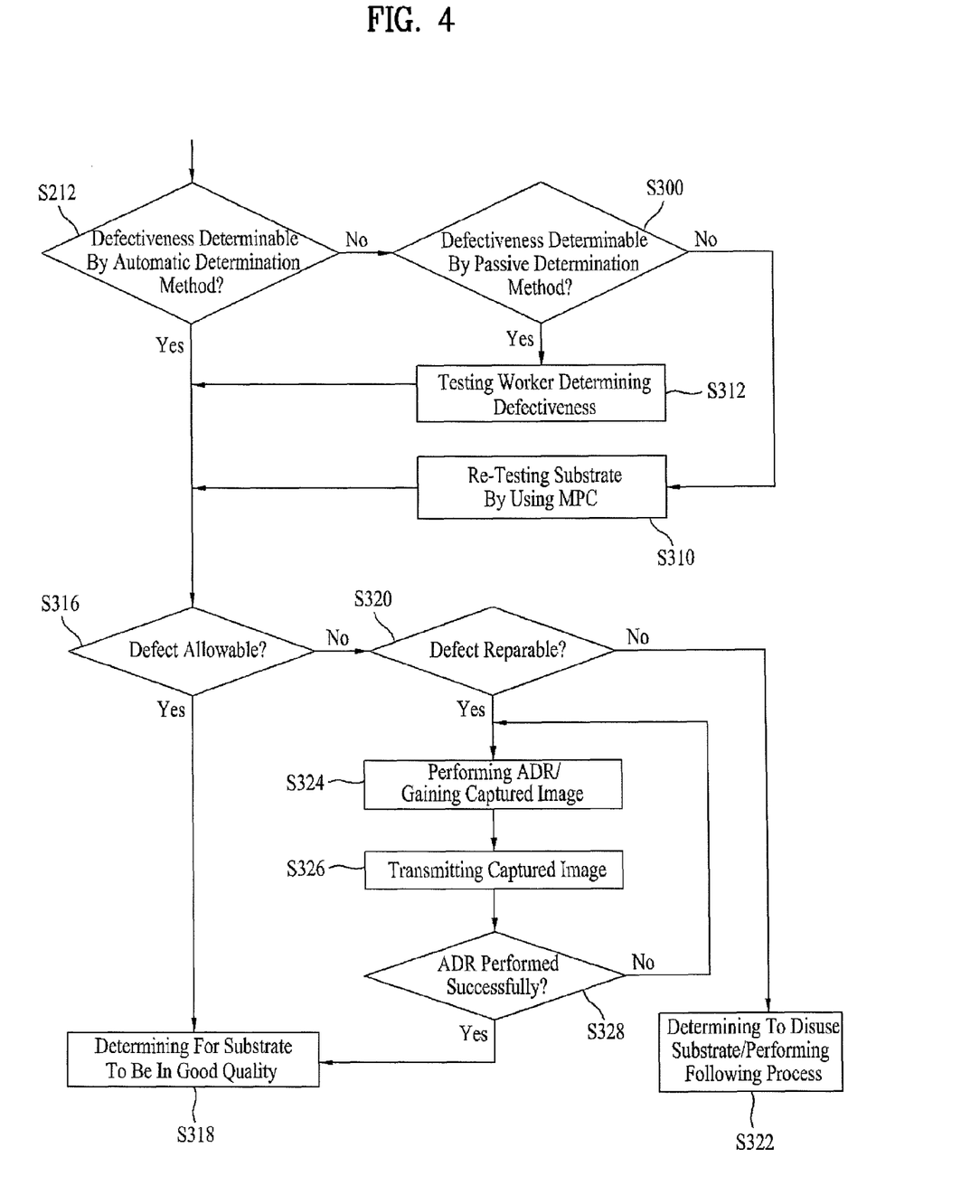
FIG. 4 is a flow chart illustrating a method of testing the LCD device of FIG. 3.

FIG. 4 is a flow chart illustrating the testing system of the LCD device according to another embodiment of the present invention.

The steps of S202 to S212 shown in FIG. 2 may be identically applicable to the testing system according to this embodiment and repeated description thereof will be omitted accordingly.

In the testing system of the LCD device according to this embodiment of the present invention, ARPC 115 determines whether defectiveness of the present substrate is determinable by the automatic determination method after the steps of S202 and S212.

If it is determined that the defectiveness of the substrate is undeterminable by the automatic determination method, it is determined whether the defectiveness is determinable by the passive determination method (S300). In contrast, if it is determined that the defectiveness is determinable by the automatic determination method, it is determined whether the degree of the defect generated in the array or color filter substrate is minute enough to be allowable (S316).

If the degree of the defect is minute enough to be allowable based on the result of the determination in the step (S316), it is determined that the substrate is good and a following process is performed (S318). In contrast, if it is determined that the degree of the defect not minute enough to be allowable, it is determined whether the defect is repairable by the ADR (S320). If it is determined that the defect is irreparable, it is determined that the substrate is defective and a following process is performed (S322). In contrast, if it is determined that the defect is repairable, the testing device 110 performs the ADR for the defect and it captures an image of an area having the ADR performed therein (S324). Here, testing device 110 transmits the information of the captured image to the main server 130. Hence, the main server 130 stores the received image in the database and it transmits the received image to the QPC 150 (S326).

Hence, the QPC 150 determines whether the defect is repaired successfully, that is, whether the ADR is performed successfully by using the captured image information of the area having the ADR performed therein (S328).

If the ADR is performed successfully, specifically, if there is no defect in the array or color filter substrate because of the successful performance of the ADR, the above step of S318 is performed to determine whether the substrate is good and then a defect testing for a next substrate may be performed. In the meanwhile, if the defect still remains even after the testing device 110 repairs the defect, that is, it is determined that the ADR is not successful, the step of repairing the defect by the testing device 110 is repeated.

If it is determined that the defectiveness is undeterminable by the automatic determination method in S212, the ARPC 115 transmits the information such as the image file of the captured defect, the defect information and the testing device number to the main server 130 and then the main server 130 transmits the information to the PRPC 140. Hence, the PRPC 140 reviews and tests the defect based on the image file of the captured defect (S316). That is, the testing worker opens and reviews the image file of the captured defect and he/she performs the defect determination process. After that, the above steps of S316 to S328 are performed to determine the defectiveness or good quality of the substrate and the following processes are performed.

Hence, if it is determined that the defectiveness of the substrate is undeterminable by the passive determination method in S300, re-testing for the defect is performed by the MPC 120 (310). Here, while the PRPC 140 reviews and performs the determination for the defect based on the image file of the captured defect, the MPC 120 reviews and performs the determination for the defect based on live images of the array or color filter substrate photographed by the camera of the testing device in real-time.

After that, as the above steps of S316 to S328 are performed, the defectiveness or good quality of the substrate is determined and a following process is performed.

The information of the defect causing the determination performed by the MPC 120 is transmitted to the ARPC 115 and it is upgraded to the defect determining automation program. As a result, if the defect causing the determination by the MPC 120 is generated again, the defect can be determined by the automatic determination method of the ARPC 115.

As mentioned above, the testing system of the LCD device according to another embodiment is able to automatically determined defectiveness of the substrate by using the ARPC 115 configured of the first to the nth PC corresponding to the first to the n device of the testing device 110. Compared with the conventional testing system performing by the passive determination method, the testing time and the number of the testing workers may be reduced remarkably. In addition, defect determination success rate may increase noticeably and thus reliability of defect testing may be improved, because the defectiveness of the substrate is determined by the automatic determination method according to the defect testing system of the present invention, not by the passive determination method performed by the testing worker.

Furthermore, only if the defect is generated which is undeterminable by the automatic determination method of the ARPC 115, the passive determination method of the PRPC 140 is performed. If the defectiveness of the substrate is undeterminable even by the passive determination method of the PRPC 140, the defectiveness is determined by using the MPC 120. As a result, the success rate of the substrate defect testing may be almost perfect and the reliability of the defect testing may be maximized.

Therefore, according to the testing system of the LCD device, defect testing is performed by the automatic determination method and only defects that are not tested by the automatic determination method are tested by a passive determination method. As a result, the testing time and the number of the testing workers may be reduced. Furthermore, the defectiveness of the substrate is determined by the automatic determination method. As a result, the defect determination success rate may increase and reliability of the defect testing may be improved.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. A system for testing a liquid crystal display (LCD) device comprising:
   a testing device photographing and capturing an image of a defect generated on a substrate having a thin film array formed thereon, the testing device providing testing information on the defect;
   an automatic review host (ARPC) automatically determining defectiveness of the substrate using a defect determining automation program, the captured image and the testing information on the defect;
   a passive review host (PRPC) passively determining defectiveness of the substrate based on the captured image and the testing information on the defect, if the defectiveness of the substrate is undeterminable by the ARPC; and
   a main server connecting the ARPC with the PRPC and storing the captured image and the testing information on the defect,
   wherein the ARPC extracts characteristics of the defect using the captured image and the testing information on the defect and the ARPC analyzes the extracted characteristics of the defect to classify and calculate the degree of the defect using a defect determining automation program.

2. The system for testing the LCD device as claimed in claim 1, wherein in case that it is determined that the degree of the defect is reparable by the ARPC, the testing device repairs the defect.

3. The system for testing the LCD device as claimed in claim 2, wherein the ARPC determines whether the defect is reparable by the testing device.

4. The system for testing the LCD device as claimed in claim 2, further comprising:
   a re-testing host (MPC) reviewing and determining the defectiveness of the substrate based on an image photographed by the testing device in real time, in case that the defectiveness of the substrate is undeterminable by the ARPC and PRPC.

5. The system for testing the LCD device as claimed in claim 2, further comprising:
   a quality managing host (QMPC) determining success of the defect repairing performed by the testing device.

6. A method for testing a LCD device comprising steps of:
   photographing a defect generated in a substrate having a thin film array formed thereon and capturing an image of the photographed defect at a testing device;
   determining reliability of the captured image at the testing device;
   reviewing the defect and extracting characteristics of the defect at an automatic review host, if it is determined that the captured image is reliable at the testing device;
   analyzing the extracted characteristics of the defect using a defect determining automation program, and classifying and calculating degree of the defect at the automatic review host;
   determining based on the result of the calculation whether the defectiveness of the substrate is determinable by the defect determining automation program at the automatic review host;
   determining the defectiveness of the substrate by the defect determining automation program at the automatic review host, if the defectiveness of the substrate is determinable at the automatic review host; and
   passively determining the defectiveness of the substrate at a passive review host the automatic review host, if the defectiveness of the substrate is undeterminable at the automatic review host.

7. The method for testing the LCD device as claimed in claim 6, wherein the step of determining the defectiveness of the substrate at the automatic review host comprises steps of:
   determining that the substrate is in good quality at the automatic review host, if the degree of the defect is allowable based on the result of the calculation and determining whether the defect is reparable at the automatic review host, if the degree of the defect is not in good quality based on the result of the calculation;
   determining to disuse the substrate at the automatic review host, if it is determined that the defect is irreparable based on the result of the determination; and repairing the defect at the testing device, if it is determined that the defect is reparable at the automatic review host.

8. The method for testing the LCD device as claimed in claim 7, wherein the step of passively determining the defectiveness of the substrate at the passive review host comprises steps of:
- determining the defectiveness of the substrate by reviewing and testing the captured image; at the passive review host
- determining to disuse the substrate at the passive review host, if it is determined that the defect is irreparable at the passive review host; and
- repairing the defect at the testing device, if it is determined that the defect is reparable at the passive review host.

9. The method for testing the LCD device as claimed in claim 7, further comprising steps of:
- photographing the defect in real time at the testing device if it is determined that the defectiveness of the substrate is undeterminable at the passive review host;
- reviewing and determining the defectiveness of the substrate at a re-testing host based on the photographed image of the substrate from the testing device;
- determining to disuse the substrate at the re-testing host, if it is determined that the defect is irreparable at the re-testing host; and
- repairing the defect at the testing device, if it is determined that the defect is reparable at the re-testing host.

10. The method for testing the LCD device as claimed in claim 9, further comprising steps of:
- capturing an image of area having the defect repair performed therein at the testing device and determining success of the repair using the captured image at a quality managing host;
- determining that the substrate is in good quality at the quality managing host, if it is determined that the defect is repaired successfully at the quality managing host; and
- repeating the repair of the defect at the testing device, if it is determined that the defect still remains at the quality managing host.

* * * * *

UNITED STATES PATENT AND TRADEMARK OFFICE
CERTIFICATE OF CORRECTION

PATENT NO. : 8,234,094 B2  Page 1 of 1
APPLICATION NO. : 12/631950
DATED : July 31, 2012
INVENTOR(S) : Ja-Geun Kim et al.

It is certified that error appears in the above-identified patent and that said Letters Patent is hereby corrected as shown below:

On the Title Page

Left column, after item (65), insert a new item as follows:

-- (30)    Foreign Application Priority Data

March 31, 2009    (NK)    10-2009-27293 --.

Signed and Sealed this
Thirteenth Day of November, 2012

David J. Kappos
*Director of the United States Patent and Trademark Office*